United States Patent
Gillies et al.

(10) Patent No.: US 6,834,201 B2
(45) Date of Patent: Dec. 21, 2004

(54) CATHETER NAVIGATION WITHIN AN MR IMAGING DEVICE

(75) Inventors: George T. Gillies, Charlottesville, VA (US); Roger N. Hastings, Maple Grove, MN (US); Jeffrey M. Garibaldi, St. Louis, MO (US); William C. Broaddus, Midlothian, VA (US)

(73) Assignee: Stereotaxis, Inc., St. Louis, MO (US)

( * ) Notice: Subject to any disclaimer, the term of this patent is extended or adjusted under 35 U.S.C. 154(b) by 0 days.

(21) Appl. No.: 10/429,524

(22) Filed: May 5, 2003

(65) Prior Publication Data

US 2003/0195412 A1 Oct. 16, 2003

Related U.S. Application Data

(62) Division of application No. 09/772,188, filed on Jan. 29, 2001, now abandoned.

(51) Int. Cl.[7] .................................................. A61B 5/05
(52) U.S. Cl. ........................................ 600/411; 600/407
(58) Field of Search ................................ 600/411, 410, 600/407, 436; 324/307, 308, 309, 310, 207, 207.11, 207.23, 207.24, 207.25, 207.26; 436/173

(56) References Cited

U.S. PATENT DOCUMENTS

| | | | |
|---|---|---|---|
| 4,809,713 A | 3/1989 | Grayzel | |
| 4,869,247 A | 9/1989 | Howard, III et al. | |
| 5,211,165 A | 5/1993 | Dumoulin et al. | |
| 5,375,596 A | 12/1994 | Twiss et al. | |
| 5,558,091 A | 9/1996 | Acker et al. | |
| 5,592,939 A | 1/1997 | Martinelli | |
| 5,606,980 A | 3/1997 | Calhoun et al. | |
| 5,622,169 A | 4/1997 | Golden et al. | |
| 5,645,065 A | 7/1997 | Shapiro et al. | |
| 5,707,334 A | 1/1998 | Young | |
| 5,713,858 A | 2/1998 | Heruth et al. | |
| 5,715,822 A | 2/1998 | Watkins et al. | |
| 5,727,553 A | 3/1998 | Saad | |
| 5,728,079 A | 3/1998 | Weber et al. | |
| 5,729,129 A | 3/1998 | Acker | |
| 5,730,129 A | 3/1998 | Darrow et al. | |
| 5,735,795 A | 4/1998 | Young et al. | |
| 5,749,835 A | 5/1998 | Glantz | |
| 5,752,513 A | 5/1998 | Acker et al. | |
| 5,762,064 A | 6/1998 | Polvani | |
| 5,779,694 A | 7/1998 | Howard et al. | |
| 5,787,866 A | 8/1998 | Sugiyama et al. | |
| 5,797,849 A | 8/1998 | Vesely et al. | |
| 5,800,352 A | 9/1998 | Ferre et al. | |
| 5,810,728 A | 9/1998 | Kuhn | |
| 5,817,017 A | 10/1998 | Young et al. | |
| 5,819,737 A | 10/1998 | Young et al. | |
| 5,833,608 A | 11/1998 | Acker | |
| 5,840,031 A | 11/1998 | Crowley | |
| 5,843,076 A | 12/1998 | Webster, Jr. et al. | |
| 5,843,153 A | 12/1998 | Johnston et al. | |
| 5,845,646 A | 12/1998 | Lemelson | |

(List continued on next page.)

OTHER PUBLICATIONS

T.P.L. Roberts et al., "Integrating X–ray Angiography and MRI for Enovascular Interventions", Nov. 2000, Medica Mundi, p. 2–9.

(List continued on next page.)

Primary Examiner—Daniel Robinson
(74) Attorney, Agent, or Firm—Harness, Dickey & Pierce, P.L.C.

(57) ABSTRACT

A method of magnetically manipulating a medical device within a body part of a human patient in conjunction with MR imaging includes applying a navigating magnetic field with magnets from the MR imaging device, and changing the magnetic moment of the medical device to change the orientation of the medical device within the body part.

21 Claims, 11 Drawing Sheets

U.S. PATENT DOCUMENTS

| | | |
|---|---|---|
| 5,865,744 A | 2/1999 | Lemelson |
| 5,868,674 A | 2/1999 | Glowinski et al. |
| 5,873,865 A | 2/1999 | Horzewski et al. |
| 5,879,297 A | 3/1999 | Haynor et al. |
| 5,883,603 A | 3/1999 | Kim |
| 5,895,401 A | 4/1999 | Daum et al. |
| 5,897,529 A | 4/1999 | Ponzi |
| 5,902,238 A | 5/1999 | Golden et al. |
| 5,906,579 A | 5/1999 | Vander Salm et al. |
| 5,908,410 A | 6/1999 | Weber et al. |
| 5,913,820 A | 6/1999 | Bladen et al. |
| 5,916,162 A | 6/1999 | Snelten et al. |
| 5,919,135 A | 7/1999 | Lemelson |
| 5,921,244 A | 7/1999 | Chen et al. |
| 5,930,329 A | 7/1999 | Navab |
| 5,938,599 A | 8/1999 | Rasche et al. |
| 5,938,602 A | 8/1999 | Lloyd |
| 5,938,603 A | 8/1999 | Ponzi |
| 5,941,858 A | 8/1999 | Johnson |
| 5,947,900 A | 9/1999 | Derbyshire et al. |
| 5,947,940 A | 9/1999 | Beisel |
| 5,951,472 A | 9/1999 | Van Vaals et al. |
| 5,951,566 A | 9/1999 | Lev |
| 5,951,881 A | 9/1999 | Rogers et al. |
| 5,952,825 A | 9/1999 | Wan |
| 5,959,613 A | 9/1999 | Rosenberg et al. |
| 5,964,705 A | 10/1999 | Truwit et al. |
| 5,964,757 A | 10/1999 | Ponzi |
| 5,967,980 A | 10/1999 | Ferre et al. |
| 5,983,126 A | 11/1999 | Wittkampf |
| 5,991,737 A | 11/1999 | Chen |
| 5,994,023 A | 11/1999 | Van Damme et al. |
| 5,997,473 A | 12/1999 | Taniguchi et al. |
| 6,002,963 A | 12/1999 | Mouchawar et al. |
| 6,006,127 A | 12/1999 | Van Der Brug et al. |
| 6,013,038 A | 1/2000 | Pflueger |
| 6,014,580 A | 1/2000 | Blume et al. |
| 6,015,414 A | 1/2000 | Werp et al. |
| 6,019,276 A | 2/2000 | Auclair |
| 6,019,725 A | 2/2000 | Vesely et al. |
| 6,019,737 A | 2/2000 | Murata |
| 6,023,636 A | 2/2000 | Wendt et al. |
| 6,058,323 A | 5/2000 | Lemelson |
| 6,083,166 A | 7/2000 | Holdaway et al. |
| 6,128,174 A | 10/2000 | Ritter et al. |
| 6,157,853 A | 12/2000 | Blume et al. |
| 6,173,199 B1 | 1/2001 | Gabriel |
| 6,216,026 B1 | 4/2001 | Kuhn et al. |
| 6,233,474 B1 | 5/2001 | Lemelson |
| 6,241,671 B1 * | 6/2001 | Ritter et al. ............... 600/427 |
| 6,304,769 B1 | 10/2001 | Arenson et al. |
| 6,364,823 B1 * | 4/2002 | Garibaldi et al. ............. 600/12 |
| 6,401,723 B1 | 6/2002 | Garibaldi et al. |
| 6,505,062 B1 * | 1/2003 | Ritter et al. ................ 600/407 |
| 6,507,751 B2 * | 1/2003 | Blume et al. ............... 600/424 |
| 6,522,909 B1 * | 2/2003 | Garibaldi et al. ........... 600/424 |
| 6,594,517 B1 * | 7/2003 | Nevo ........................ 600/411 |

OTHER PUBLICATIONS

Seeber, "Triaxial magnetic field gradient system for micro-coil magnetic resonance imaging", Nov., 2000, Reviwe of Scientific Instruments, vol. 71, No. 11, p. 4263–4272.

Coutts et al., "Integrated and Interactive Position Tracking and Imaging of Interventional Tools and Internal Devices Imaging Small Fiducial Receiver Coils", Mar., 1999, ROMAC, pp. 908–913.

Burl et al., "Twisted–Pair RF Coil Suitable for Locating the Track of a Catheter", 1999, Magnetic Resonance in Medicine, 41, pp. 636–638.

Worley, "Use of a Real–Time Three–dimensional Magnetic Navigation System for Radiofrequency Ablation of Accessory Pathways", Aug. 1999, PACE, vol. 21, pp. 1636–1645

Nakamura et al., "A Prototype Mechanism for Three–Dimensional Levitated Movement of a Small Magnet", Mar., 1997 Transactions of Mechatronics, vol. 2, No. 1, pp. 41–50.

Bakker et al., "MR–guided Endovascular Interventions: Susceptibility–based Catheter and Near–Real–Time Imaging Technique", Radiology, Nov., 1997, pp. 273–276.

Rasche et al., "Catheter Tracking Using Continuous Radial MRI", Nov., 1997, MRM, vol. 37, pp. 963–968.

Wildermuth et al., "MR Imaging–guided Intravascular Procedures: Initial Demonstration in a Pig Model", Radiology, Feb., 1997, pp. 578–583.

Planert et al., "Measurements of magnetism–related forces and torque moments affecting medical instruments, implants, and foreign objects during magnetic resonance imaging at all degrees of freedom", Jun., 1996, Med. Phys, vol. 23, pp. 851–856.

Manner et al., "MR Imaging in the Presence of Small Circular Metallic Implants", ACTA Radiological, 1995, pp. 551–554.

Gillies et al., "Magnetic manipulation instrumentation for medical physics research", Mar., 1994, Rev. Sci. Instrum., vol. 65, pp. 533–562.

T.P.L. Roberts et al., "Remote control of Catheter Tip Defelction: An Opportunity for Interventional MRI", Magnetic Resonance in Medicine, 48: 1091–1095 (2002).

* cited by examiner

CATHETER NAVIGATION WITHIN AN MR IMAGING DEVICE

CROSS-REFERENCE TO A PRIOR APPLICATION

This application is a divisional of U.S. patent application Ser. No. 09/772,188, filed Jan. 29, 2001, now abandoned the disclosure of which is incorporated by reference.

FIELD OF THE INVENTION

This invention relates to an apparatus for navigating medical devices within the body to sites of treatment delivery, and methods of using this apparatus to achieve this navigation. More specifically, this invention relates to the use of a magnetic field from an MR imaging device to navigate a magnetic medical device within the body.

BACKGROUND OF THE INVENTION

The need for improved surgical navigation techniques stimulated the development of magnetic stereotaxis as a novel means for guiding a surgical implant, such as a catheter, along nonlinear paths within a body part. In particular, it is useful in intraparenchymal applications within the brain, where linear stereotactic techniques (either framed or frameless) do not permit the probe to follow single-pass curvilinear paths to a target location deep within the brain, as first taught by Howard et al. in U.S. Pat. No. 4,869,247 incorporated herein by reference. Howard et al. subsequently taught magnetic stereotactic techniques for volume-contoured therapy delivery within the brain and elsewhere in the human body in succeeding U.S. Pat. Nos. 5,125,88, 5,707,334, and 5,779,694 incorporated herein by reference. Advanced versions of magnetically guided surgical systems capable of performing magnetic stereotactic procedures in the brain and in other body parts have been disclosed in U.S. patents by Werp et al., U.S. Pat. No. 5,9331,818; Blume et al., U.S. Pat. No. 6,014,580; Werp et al., U.S. Pat. No. 6,015,414; Ritter et al., U.S. Pat. No. 6,128,174; and Blume et al., U.S. Pat. No. 6,157,853. In all of these approaches, as well as in any of the other known techniques for magnetic manipulation of a probe mass or implant located within the body (see Gillies et al., "Magnetic manipulation instrumentation for medical physics research," *Review of Scientific Instruments*, pp. 533–562 (USA 1994)), incorporated herein by reference, the controlled movement of the probe mass or implant is actuated by a magnetic field created external to the body. In all such arrangements the magnetic component of the implant (typically located at the tip of a catheter) is a passive ferromagnetic or permanent magnetic element of a geometry consistent with that of the catheter's form and function, and within which there either exists or can be made to exist, adequate magnetic moment to create the forces and torques needed to steer and/or guide the implant within the body part into which it has been inserted.

Magnetic stereotaxis is particularly useful for navigation of medical devices throughout body tissues, cavities, and vessels. Discussion of applications to catheter navigation within the chambers of the heart for electrophysiologic mapping and ablation can be found in Hall et al., U.S. patent application Ser. No. 09/405,314, incorporated herein by reference. Disclosure of navigation of catheters within the myocardial tissue of the heart can be found in Sell et al., U.S. patent application Ser. No. 09/398,686, incorporated herein by reference. Removal of tissues from body lumens and cavities via magnetic navigation of atherectomy tools is disclosed in Hall et al., U.S. patent application Ser. No. 09/352,161, incorporated herein by reference. Catheters for magnetic navigation within the blood vessels of the brain and other body parts are disclosed in Garibaldi, U.S. patent application Ser. No. 60/153,307, incorporated herein by reference.

Four inherent limitations to this general design of magnetic stereotaxis system are the following. First, it is generally unsafe to perform magnetic resonance (MR) imaging studies during or after a magnetic stereotaxis procedures in which the magnetic element of the implant is still resident within the patient, as might be contemplated in situations where updated MR data might be needed for ongoing magnetic stereotaxis navigation requirements. This is because the large fields intrinsic to all types of MR scanners (either standard bore-type systems or the lower-field interventional-style systems) are large enough to cause otherwise uncontrolled displacement of the implant within the patient. The nature of this particular problem is discussed in the broader context of MR-driven forces on implants, by Planert et al., "Measurements of magnetism-related forces and torque moments affecting medical instruments, implants, and foreign objects during magnetic resonance imaging at all degrees of freedom," *Medical Physics*, pp. 851–856 (USA 1996) and by Manner et al., "MR Imaging in the presence of small circular metallic implants," *Acta Radiological*, pp. 551–554 (Denmark 1996), the disclosures of both of which are incorporated herein by reference.

A second limitation of the existing art is that relatively complex arrangements of magnetic field sources external to the patient must be assembled and controlled in order to carry out magnetic stereotactic movement of the implant. A single static background field is virtually always inappropriate for effecting controlled movement of the magnetic element in the implant used in existing magnetic stereotaxis procedures. A third limitation, related to the second, is that a magnetic element left in the brain or another body part can create a significant imaging artifact when that body part is imaged by an MR scanner, most typically rendering that imaging data set useless or of greatly reduced diagnostic and therapeutic value to the clinician and patient.

A fourth limitation is that appreciably and clinically precious time could be lost when carrying out a sequential and reciprocal process of conducting a magnetic stereotaxis procedure that must be interleaved with intra-operative MR imaging studies for diagnostic, therapeutic or navigational purposes. These limitations are not traversed by Kucharczyk et al. in their U.S. patent application Ser. No. 09/174,189 and in their International Application No. PCT/US99/24253, (the disclosure of both of which are incorporated herein by reference), which teach means for serial and reciprocal movement of the patient from a magnetic stereotaxis system to an MR scanner for purposes of updating the imaging information used for the reference portion of the magnetic stereotaxis procedure.

A more nearly ideal situation would arise if it were possible to integrate the form and function of a MR scanner and a magnetic stereotaxis system in such a way that magnetic stereotaxis procedures could be carried out within an MR scanner (or vice versa), and all done in such a way that the form and function of the MR scanning process would not interfere with those of the magnetic stereotaxis process, but that the respective forms and functions would instead complement and/or enhance each other. The subject of the present invention is a means and technique that accomplishes this goal and circumvents the existing limitations by incorporating a triaxial arrangement of miniature electromagnets as the magnetic element at the tip of the medical device or catheter. By externally regulating the electrical currents that pass through each of the independent coils, the torque and force on the tip of the medical device or catheter can be made to react to a static magnetic field of a MR scanner in such a way that the tip of the medical device or catheter can be guided along a preferred path to reach a target location within a brain or other body part. The resulting means and technique will thus exhibit all of the advantages of conventional magnetic stereotaxis (primarily the ability to navigate the medical device or catheter along complex curvilinear paths), while incorporating the further advantages of rapid sequential MR imaging of the patient, without introducing imaging artefacts on the MR images, since imaging is performed during periods when no currents flow through the triaxial coil components.

Medical devices with one or more miniaturized coils on them have been disclosed for a variety of other purposes, but none have been designed for use as the actuator in a combined magnetic stereotaxis and MR imaging process such as the type that is the subject of the present invention. Instead, such coil systems have been limited in function to identifying the location of the probe (in which they are housed) in relation to the body part into which the probe is inserted. Examples of such disclosures include Grayzel, U.S. Pat. No. 4,809,713; Dumoulin et al., U.S. Pat. No. 5,211,165; Twiss et al., U.S. Pat. No. 5,375,596; Acker et al., U.S. Pat. No. 5,558,091; Martinelli, U.S. Pat. No. 5,592,939; Calhoun et al., U.S. Pat. No. 5,606,980; Golden et al. U.S. Pat. No. 5,622,169; Shapiro et al., U.S. Pat. No. 5,645,065; Heruth et al., U.S. Pat. No. 5,713,858; Watkins et al., U.S. Pat. No. 5,715,822; Saad, U.S. Pat. No. 5,727,553; Weber et al., U.S. Pat. No. 5,728,079; Acker, U.S. Pat. No. 5,729,129; Darrow et al., U.S. Pat. No. 5,730,129; Young et al., U.S. Pat. No. 5,735,795; Glantz, U.S. Pat. No. 5,749,835; Acker et al., U.S. Pat. No. 5,752,513; Slettenmark, U.S. Pat. No. 5,758,6670; Polvani, U.S. Pat. No. 5,762,064; Kelly et al., U.S. Pat. No. 5,787,886; Vesely et al., U.S. Pat. No. 5,797,849; Ferre et al. U.S. Pat. No. 5,800,352; Kuhn, U.S. Pat. No. 5,810,728; Young et al., U.S. Pat. No. 5,817,017; Young et al., U.S. Pat. No. 5,819,737; Kovacs, U.S. Pat. No. 5,833,603; Crowley, U.S. Pat. No. 5,840,031; Webster, Jr. et al., U.S. Pat. No. 5,843,076; Johnston et al., U.S. Pat. No. 5,843,153; Lemelson, U.S. Pat. No. 5,845,646, Lemelson, U.S. Pat. No. 5,865,744; Glowinski et al., U.S. Pat. No. 5,868,674; Horzewski et al., U.S. Pat. No. 5,873,865; Haynor et al., U.S. Pat. No. 5,879,297; Daum et al., U.S. Pat. No. 5,895,401; Ponzi, U.S. Pat. No. 5,897,529; Golden et al., U.S. Pat. No. 5,902,238; Vander Salm et al., U.S. Pat. No. 5,906,579; Weber et al., U.S. Pat. No. 5,908,410; Lee et al., U.S. Pat. No. 5,911,737; Bladen et al., U.S. Pat. No. 5,913,820; Snelten et al., U.S. Pat. No. 5,916,162; Lemelson, U.S. Pat. No. 5,919,135; Chen et al., U.S. Pat. No. 5,921,244; Navab, U.S. Pat. No. 5,930,329; Rasche et al., U.S. Pat. No. 5,938,599; Lloyd, U.S. Pat. No. 5,938,602; Ponzi, U.S. Pat. No. 5,938,603; Johnson, U.S. Pat. No. 5,941,858; Cermak. U.S. Pat. No. 9,941,889; Johnson et al., U.S. Pat. No. 5,944,023; Derbyshire et al., U.S. Pat. No. 5,947,900; Beisel, U.S. Pat. No. 5,947,940; Van Vaals et al., U.S. Pat. No. 5,951,472; Lev, U.S. Pat. No. 5,951,566; Rogers et al., U.S. Pat. No. 5,951,881; Wan, U.S. Pat. No. 5,952,825; Rosenberg et al., U.S. Pat. No. 5,959,613; Ponzi, U.S. Pat. No. 5,964,757; Ferre et al., U.S. Pat. No. 5,967,980; Wittkampf, U.S. Pat. No. 5,983,126; Taniguchi et al., U.S. Pat. No. 5,997,473; Mouchawar et al., U.S. Pat. No. 6,002,963; Van Der Brug et al., U.S. Pat. No. 6,006,127; Pflueger, U.S. Pat. No. 6,013,038; Vesely et al., U.S. Pat. No. 6,019,725; Webb, U.S. Pat. No. 6,019,726; Murata, U.S. Pat. No. 6,019,737; Wendt et al., U.S. Pat. No. 6,023,636; and Holdaway et al., U.S. Pat. No. 6,083,166. The disclosures of all of the foregoing are incorporated herein by reference. Other uses for miniature coils or microcoils on catheters include the controlled introduction of local electromagnetic fields during the MR imaging process for the purpose of improving imaging contrast in the tissues adjacent to the catheter or probe, as taught for instance by Truwit et al., U.S. Pat. No. 5,964,705, incorporated herein by reference. Miniature triaxial arrangements for field sensing in medical probes have been disclosed by Acker, U.S. Pat. No. 5,833,608, incorporating herein by reference. Additional publications that document related uses for microcoils on catheters for either tracking or imaging purposes include the papers of Wildermuth et al., "MR Imaging-guided intravascular procedures: initial demonstration in a pig model," *Radiology*, 578–583 (USA 1997), Bakker et al., "MR-guided endovascular interventions: susceptibility-based catheter and near-real-time imaging technique," *Radiology*, pp. 273–276 (USA 1997), Rasche et al., "Catheter tracking using continuous radial MRI," *MRM*, pp. 963–968 (USA 1997), Worley, "Use of a real-time three-dimensional magnetic navigation system for radiofrequency ablation of accessory pathways," *PACE*, pp. 1636–1645 (USA 1998), Burl et al., "Twisted-pair RF coil suitable for locating the track of a catheter," *MRM*, pp. 636–638 (USA 1999) and Coutts et al, "Integrated and interactive position tracking and imaging of interventional tools and internal devices using small fiducial receiver coils," *MRM*, pp. 908–913 (USA 1998). The disclosures of which are incorporated by reference. Coils in the catheter tip can be used to both locate the tip, and to measure the orientation of the tip in three dimensional space, as discussed by Shapiro et al, U.S. Pat. No. 5,645,065, and Haynor et al, U.S. Pat. No. 5,879,297, the disclosures of which are incorporated by reference.

SUMMARY OF THE INVENTION

The invention relates to the interaction between the static magnetic field of an MR scanner and one or more independent magnetic dipole moments created by a plurality of electromagnetic elements that are located within a medical device or catheter within a patient. The concept of utilizing a variable magnetic moment in the tip of a catheter for navigation in a static magnetic field was disclosed by Garibaldi et al., U.S. patent application Ser. No. 09/504,835, which is incorporated herein in its entirety by reference. Garibaldi et al. discusses a variety of permanent and electromagnetic means for generating a variable moment at the catheter tip for navigation in a static field, which may be energized for the purpose of navigation. The present invention employs the static field of an MRI imager, and the combined sequential processes of navigation and MRI imaging. Our discussion focuses on the static field of an MR imager which is always on, and for practical purposes cannot be turned off or otherwise changed or interrupted. For this reason, the present invention cannot employ permanent or inducible magnetic materials within the medical device. Consequently, the variable moment must be generated by coils, and preferably air-core coils.

If a static magnetic field H is acting along the z direction of the bore of a MR imaging, and a magnetic dipole moment m is present in the magnetic element of an implanted probe or catheter, then the vectors representing H and m in a three-dimensional space can be written $H=Hk$ along the z-axis and $m=m_x i+m_y j+m_z k$ and the torque experienced by the dipole moment in the field of the MR scanner is $\tau = m \times H$.

The x, y, and z components of the moment m are controlled independently, so that the vector m can point in any arbitrary direction in three dimensional space.

Evaluation of the vector cross product produces the components $\tau_x=m_yH$, $\tau_y=-m_xH$, and $\tau_z=0$. The torque acting on the dipole is perpendicular to m and H and in this case has no component about the z-axis along which the magnetic field lies. It is possible, however, to navigate a catheter to points lying in the plane perpendicular to H via successive small displacements of the moment out of this plane. This process can be referred to as compound rotation about the H axis. The first step in the process is to rotate the catheter tip upward out of the x-y plane at an angle which advances the catheter projection on the x-y plane, followed by a second rotation which rotates the catheter back down to the x-y plane, while once again advancing the catheter orientation angle. The net rotation of the catheter tip about the z-axis thus follows a sawtooth or triangular trajectory, each step in the advancement being made up of two allowed out-of-plane rotations.

One can make numerical estimates of the sizes of the torques that can act on the dipole in the presence of the MR scanner field by noting that the magnitude of the torque is given by expanding the cross product $\tau=m \times H$ to obtain $\tau=mH \cos\theta$ where $\theta$ is the angle between m and H. $\tau$ is a maximum when $\theta=90°$. If the dipole moment is produced by a coil that has N turns of wire windings carrying an electrical current I, and has a cross-sectional area A, then the expression for the torque acting on the coil can be written as $\tau=NIAB$ where $B=\mu_oH$ defines the relationship between the magnetic induction B and the magnetic field strength H, with $\mu_o$ being the permeability of free space. As a practical example of the application of these principles in a clinically realistic setting, the mechanical torque required to rotate a dipole moment produced by 350 turns of wire carrying 1.4 A of current and having a diameter of 2 mm with associated cross-sectional area of $3.14 \times 10^{-6}$ m$^2$ would be $2.3 \times 10^{-3}$ N-m or 230 gram-mm in a MR scanner field of 1.5 T. If this coil is 5 mm long, the effective force couple producing the torque is 230/5=46 grams, which is adequately large for catheter navigation.

In the preferred embodiment of the present invention, three miniaturized coils of appropriate length, radius and current carrying capacity are assembled into a triaxial configuration in which the cross-sectional planes of each are orthogonal to those of the others. There are a number of different ways of doing this. In one preferred embodiment, the coils are wound on a common hollow coil form or mandrel in the shape of a rectangular parallelepiped that is made from non-conducting, non-susceptible materials which are MR compatible. In one embodiment, the coils are approximately 1 cm in length, have a diameter of 2 mm and a thickness of 0.25 mm. One transverse coil is wound around a long axis of the parallelepiped mandrel, a second transverse coil is wound along the other long axis perpendicular to the first, and the third (axial) coil is wound around the other two. The latter coil has a similar cross sectional area times number of turns as the transverse coils, so that all three coils have approximately equal dipole moment magnitude for equal energizing currents. This assembly is fixed inside the tip of a supple catheter with the leads from the coils brought down the internal length of the catheter tube to an exit point at which they are connected to three independent power supplies, one for each coil.

Cooling water or some other heat exchange medium can be made to flow through an internal jacket inside the catheter, thus bathing the triaxial coil assembly and carrying away a substantial amount of the heat generated during operation of the independent coils. The amount of cooling power available to the coils limits the level of current flow and ohmic heating that they can sustain; for example 16 W of cooling would establish a limit of 2.3 A maximum per coil assuming that the total resistance of a given coil is approximately 3Ω. The pressure driving the flow would ideally be 100 psi or less, with the flow entering the catheter at body temperature and leaving it at some higher temperature governed by considerations of patient safety and comfort.

With the coils being open circuit at the beginning of a procedure, the patient is imaged, and the location of the catheter noted. The coils themselves, rather than being passive open circuit coils, could actually serve as pick up coils for the MRI rf signal, providing an enhanced image at the site of the catheter, as discussed in the cited literature. Following this essentially real time imaging, the coils are energized, following the predictions of a coil-current vs. torque algorithm that would determine the catheter's directional advancement within the MR scanner's field, thus permitting the tip of the catheter to be steered along a desired direction. Subsequent imaging sequences are then carried out to verify the new location of the catheter's tip, and the next movement sequence is then planned and executed.

In some modem MRI machines, the patient can actually be rotated during a procedure relative to a transverse MRI magnetic field residing in a gap between magnets. Such patient rotations may be employed to further enhance navigation. In particular, the patient may be rotated in these machines to ensure that maximum torque can always be applied about directions that would otherwise be parallel with the MRI field.

Using this means and technique, catheters can be manipulated through a body part, for example the brain, and positioned such that the lumen of the catheter is left along a curvilinear path that might be optimized for contoured drug delivery for the treatment of a neurodegenerative disorder intrinsic to the brain. Many other possible scenarios can also be achieved in the same way, for instance the nonlinear stereotactic guidance of an electrode for recording of potentials, ablation of a zone of tissue or deep brain stimulation for pain or tremor control. Likewise, electrophysiological mapping and ablation procedures can be carried out within the chambers of the heart. We note that the cooling required to adequately energize the coils can also cool the electrode tip of an ablation catheter. Such cooling results in larger ablative lesions, with fewer complications associated with clot formation on the electrode tip. Steering of catheters and devices can also be carried out within the endovascular system, for diagnostic and therapeutic purposes.

A host computer can coordinate and control the power supplies used to drive the individual coils, interpreting instruction from a clinician operating an intuitive interface such as a joy stick. The control algorithm requires as input the present orientation of the triaxial coil assembly within the patient, the direction and magnitude of the MR scanner field at the location of the triaxial coil assembly, the desired new angular orientation or curvilinear displacement that is to be taken in the next step in the movement sequence, and any related anatomical or physiological information about the patient as might be required to safely and efficaciously carry out the procedure.

DETAILED DESCRIPTION OF THE INVENTION

Figure 1:
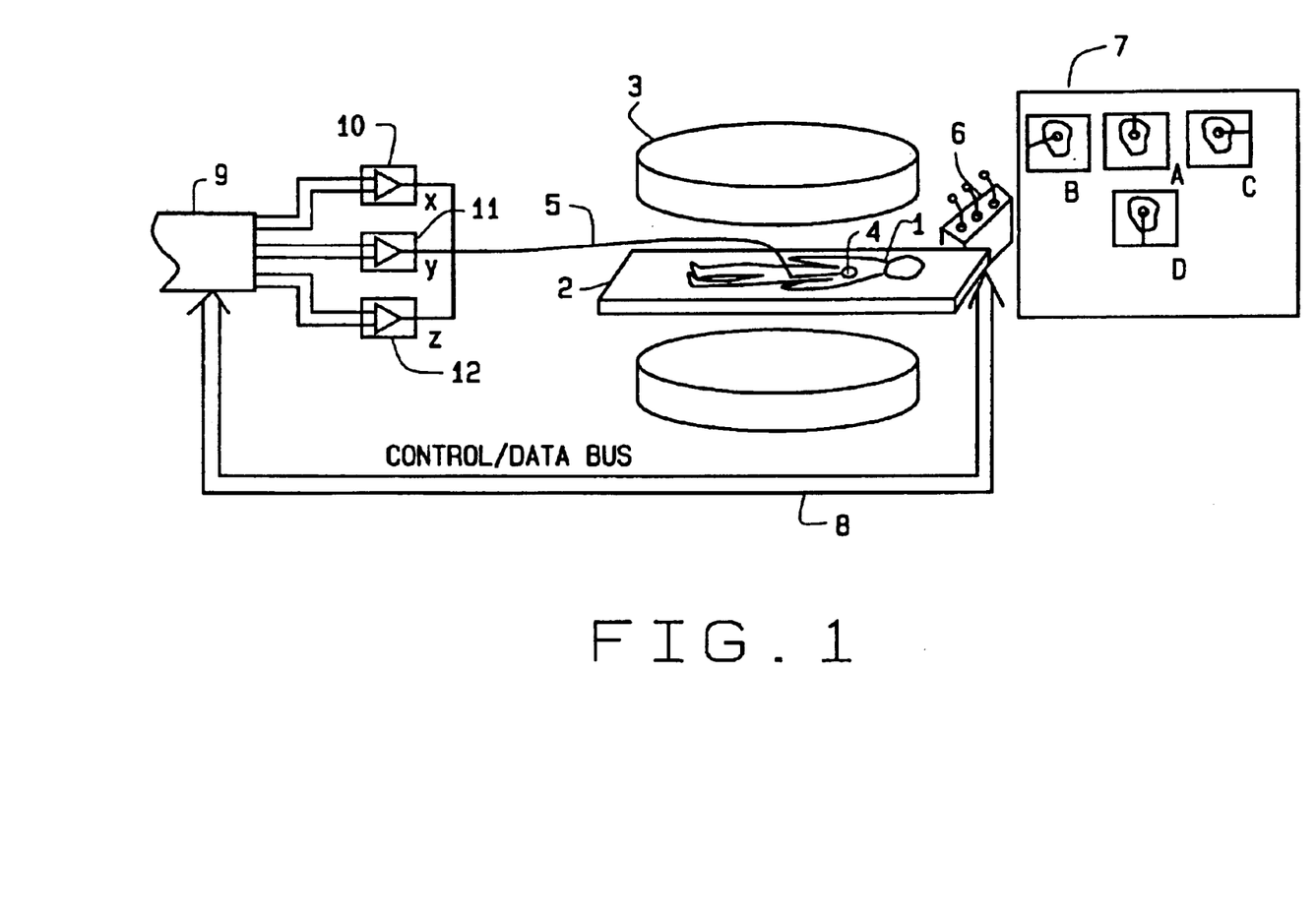
FIG. 1 is a schematic diagram of a system for implementing the method of this invention.

Referring to the drawings, FIG. 1 is a schematic of a system for carrying out a stereotactic procedure in accordance with the method of this invention. A patient 1 rests on the gurney or transport table 2 of an interventional MR imager 3, as supplied, for example, by Fonar Corp., Melville, N.Y. The procedure might alternatively be carried out inside the bore of a standard high field MR scanner, as supplied, for example, by Philips Medical Systems, Best, The Netherlands. A catheter 4 is disposed within the body of the patient 1. Leads 5 from the catheter 4 are connected to the power supplies or amplifiers 10, 11, 12 each of which drives one of three coils located inside the tip of the catheter 4. The power supplies 10, 11, 12 are controlled by an algorithm resident in the host computer 9. The physician (not shown) views the location of the catheter tip inside the body and the structure of the body part on the monitors 7 of the MR scanner 3. The monitors 7 show the sagittal, axial and coronal views and a composite three-dimensional view of the body part and the location of the catheter's tip. The physician adjusts the controls 6 that determine the parameters operating in the host computer's algorithm, in such a way that the next desired location or orientation of the catheter's tip is projected on the monitors 7. The physician then implements the motion sequence by activating the algorithm, and then observes the new location of the catheter's tip on the monitors 7. The surgeon or physician's instructions are conveyed from the control panel 6 to the host computer 9 over the system's control/data bus. Alternatively, the physician can pre-plan the path of the catheter tip on a suitable interface, and the catheter can then be directed along the desired path entirely under computer control.

Figure 2A:
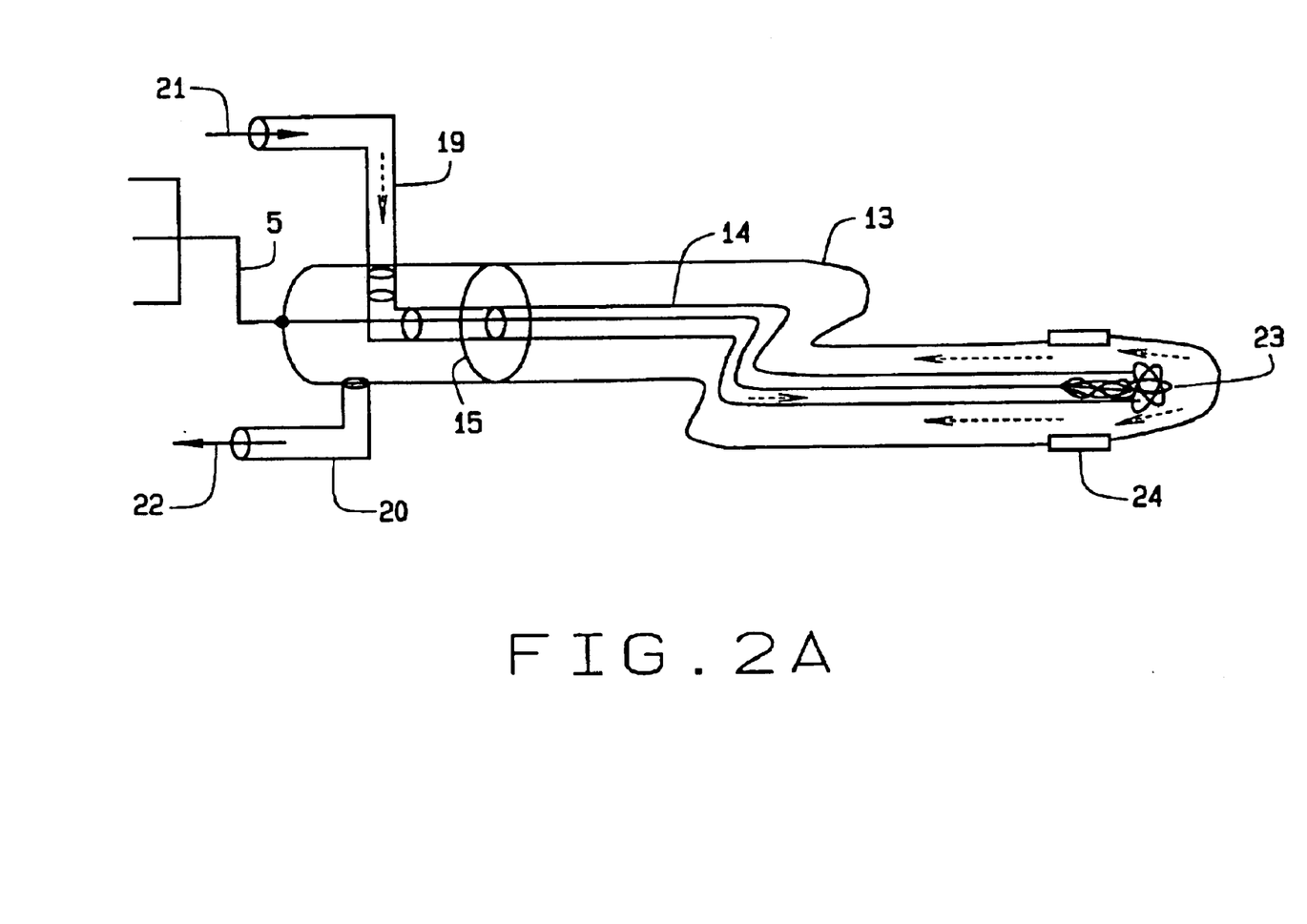
FIG. 2a is a schematic diagram of a catheter adapted for use with the method of this invention.
Figure 2B:
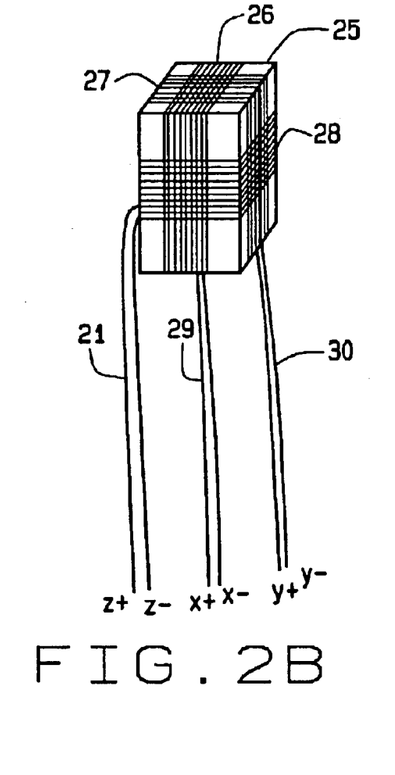
FIG. 2b is a schematic diagram of a triaxial coil system wound on a rectangular parallelepiped coil form or mandrel.
Figure 2C:
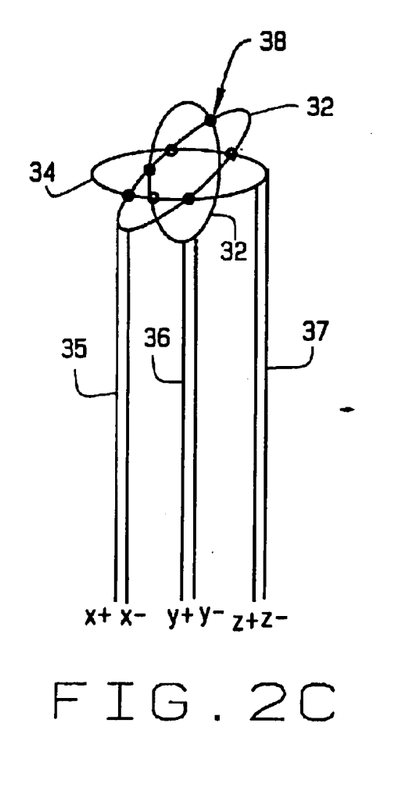
FIG. 2c is a schematic diagram of the structure of a triaxial coil system formed from the nesting together of three orthogonally oriented planar coils each having a circular cross section.

FIG. 2a is a schematic view of a catheter (4 in FIG. 1). An outer lumen 13 houses an inner lumen 14. A triaxial coil 23 is located inside the tip of the inner lumen 14 near the distal end of the outer lumen 13. The distal end of the outer lumen 13 is coupled to the main body of the outer lumen via a soft and pliable coupling 24 that permits easy and rapid articulation of the distal end. The proximal end of the outer lumen 13 connects to cooling water inlet tube 19 which is connected to a source of cooling water 21. The inner lumen 14 of the catheter 4 is connected to the water inlet tube 19 by a tubular means 15 internal to the outer lumen 13. The proximal end of the outer lumen 13 also connects to cooling water outlet tube 20 through which the flux of cooling water 22 flows. The leads 5 from the triaxial coil 23 extend from the proximal end of the catheter's outer lumen 13 and are separated into three pairs 16, 17, 18 one for each of the microcoils in the triaxial coil. FIG. 2b shows one preferred embodiment of the triaxial coil 23 based on a rectangular parallelepiped coil frame 25 on which are wound orthogonally oriented microcoils 26, 27, 28 each of which has one pair of the jumper wires 29, 30, 31 that make contact with one of the corresponding pair of the set of lead wires 5 that then run the length of the inner lumen 14. The lead wires 5 can alternatively pass through lumen 14, or be embedded in the material making up the various walls of the catheter. FIG. 2c shows another preferred embodiment of a triaxial coil 23 in which three sets of windings 32, 33, 34 having circular cross sections are nested together with their planes orthogonal to each other, and with the assembly held together by glue means 38. Each of the coil means 32, 33, 34 has one pair of jumper wires 35, 36, 37 that make contact with one of the corresponding pair of the set of lead wires 5 that then run the length of the inner lumen 14.

Figure 3A:
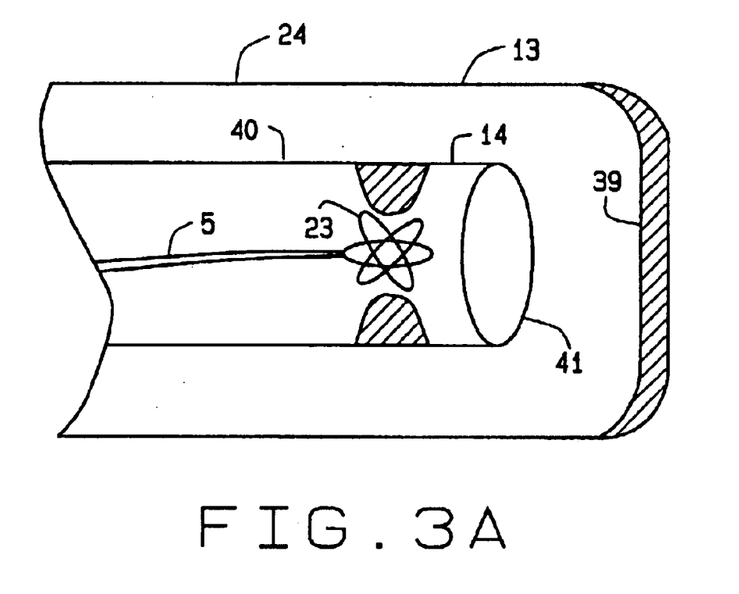
FIG. 3a is an enlarged partial longitudinal cross-sectional view of the distal tip of a catheter adapted for use in the method of this invention.
Figure 3B:
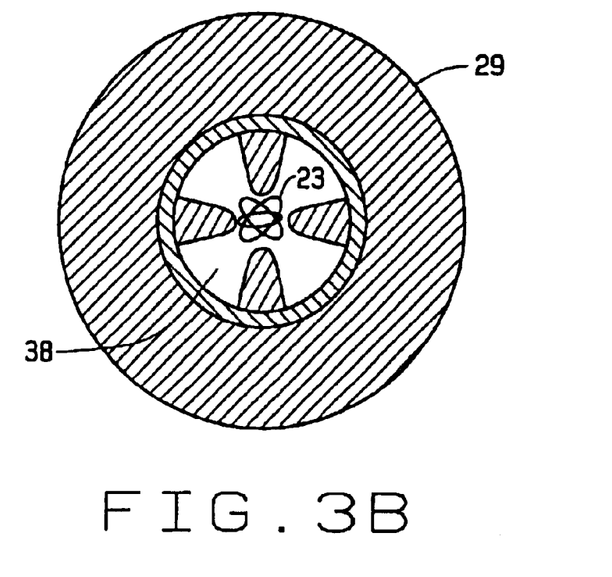
FIG. 3b is an enlarged transverse cross-sectional view of the distal tip of a catheter, adapted for use in the method of this invention; adapted for fluid cooling.

FIG. 3a shows one embodiment of the distal tip of the catheter. The outer lumen 13 and the soft pliable coupling section 24 of the wall of the outer lumen form the containment for the return flow path of the cooling water that arrives at the distal tip by flowing through the inner lumen 14. The distal end of the inner lumen 14 also has a section of soft pliable coupling material 40 that (like the segment 24) facilitates the articulation of the catheter's tip for steering purposes. The outlet port 41 for the cooling water at the distal end of the inner lumen 14 is located in close proximity to the inside surface of the distal end of the outer lumen 13. The distal tip of the catheter 39 may be constructed from a radio-opaque material or be coated on its inside surface with a layer of material 39 that is radio-opaque and MR-visible for imaging purposes. The tip 39 may also serve as an ablation electrode, which is cooled during ablation by cooling water circulating through lumens 13 and 14. One embodiment of the triaxial coil assembly 23 with its leads 5 is shown in place at the distal end of the inner lumen 14. A mounting mechanism 38 holds the triaxial coil assembly in place within the inner lumen 14.

Figure 4:
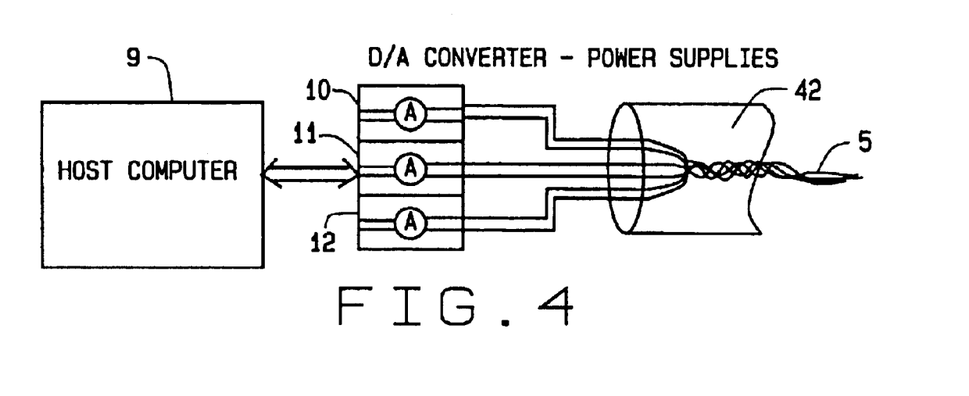
FIG. 4 is a schematic diagram of the electrical connections and components for a system for implementing the method of this invention.

FIG. 4 shows a block diagram of some details of the power handling part of the system. The host computer 9 for the system is connected by the usual data bus to the power supplies 10, 11, 12 that drive currents through the triaxial coil assembly. Each power supply has digital input and analog output hence must have an integral digital to analog converter and a means for monitoring the current as indicated. The leads from the power supply might be brought forward in twisted pairs 42 to minimize the effects of magnetic field couplings that might drive extraneous currents through them. The twisted pairs connect with the leads 5 of the triaxial coil assembly. During the MRI imaging step, the host computer 9 may receive and/or transmit rf signals from the coils 23 via leads 42 to enhance the local MRI image and/or to measure the location and orientation of the coils.

Figure 5:
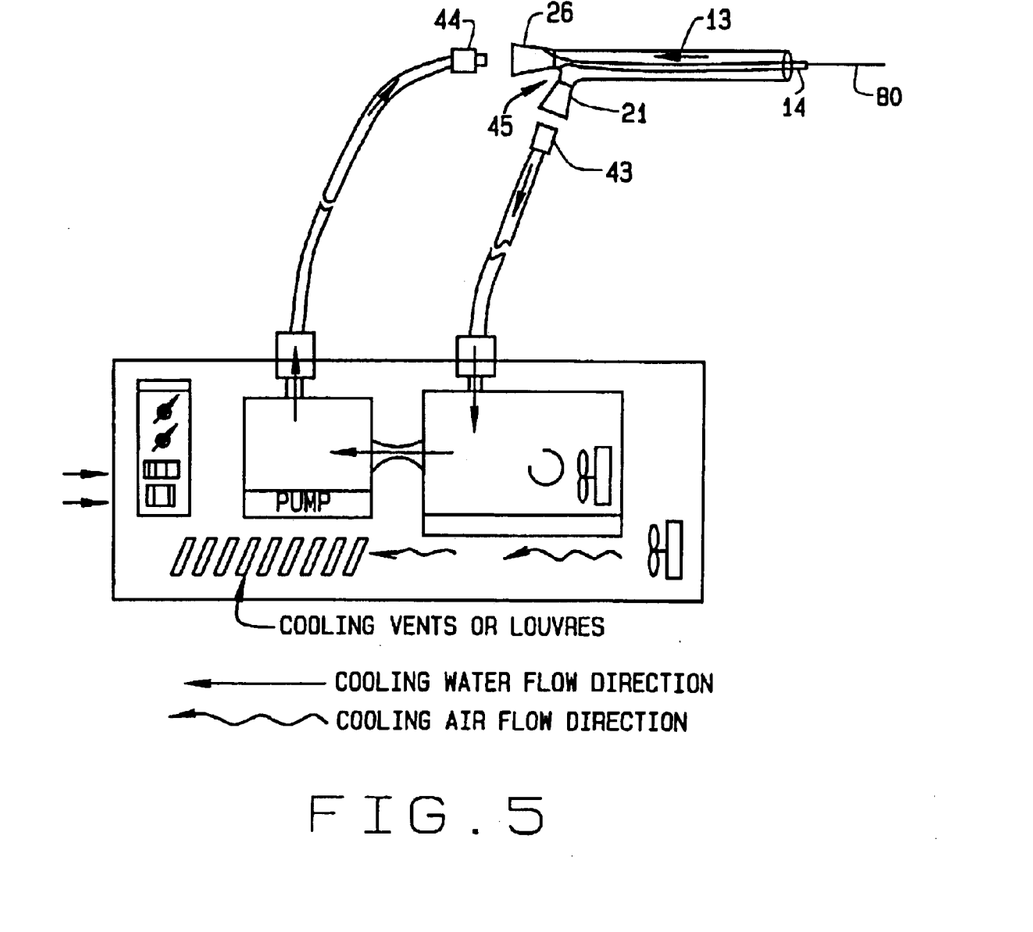
FIG. 5 is a schematic diagram of a cooling system adapted for use in the system for implementing the method of this invention.

FIG. 5 shows some additional details of the cooling water connections. The inner lumen 14 of the catheter 4 conveys the cooling water to the triaxial coil means. The inlet connection is made via the coupling tube 20. The input port 44 on the coupling tube is hooked to a source of the cooling water. Inside the coupling tube 20 is a temperature sensor 45 the leads of which traverse the wall of the coupling tube and are connected to the temperature monitor 46 to read the inlet water temperature. A reciprocal arrangement is placed on the outlet side, where the outlet water temperature is measured at its highest point, at the coil set 23. An outlet coupling tube 21 is connected to the catheter's outer lumen 13. The outlet port 43 of the outlet coupling tube 21 allows the water to exit the coupling tube and flow into a drain, or be continuously recirculated. A temperature sensor 47 monitors the outlet water temperature at the coils 23, and its leads pass through the wall of the tube and are connected to the temperature monitor 48 that is used to read the outlet water temperature.

Figure 6:
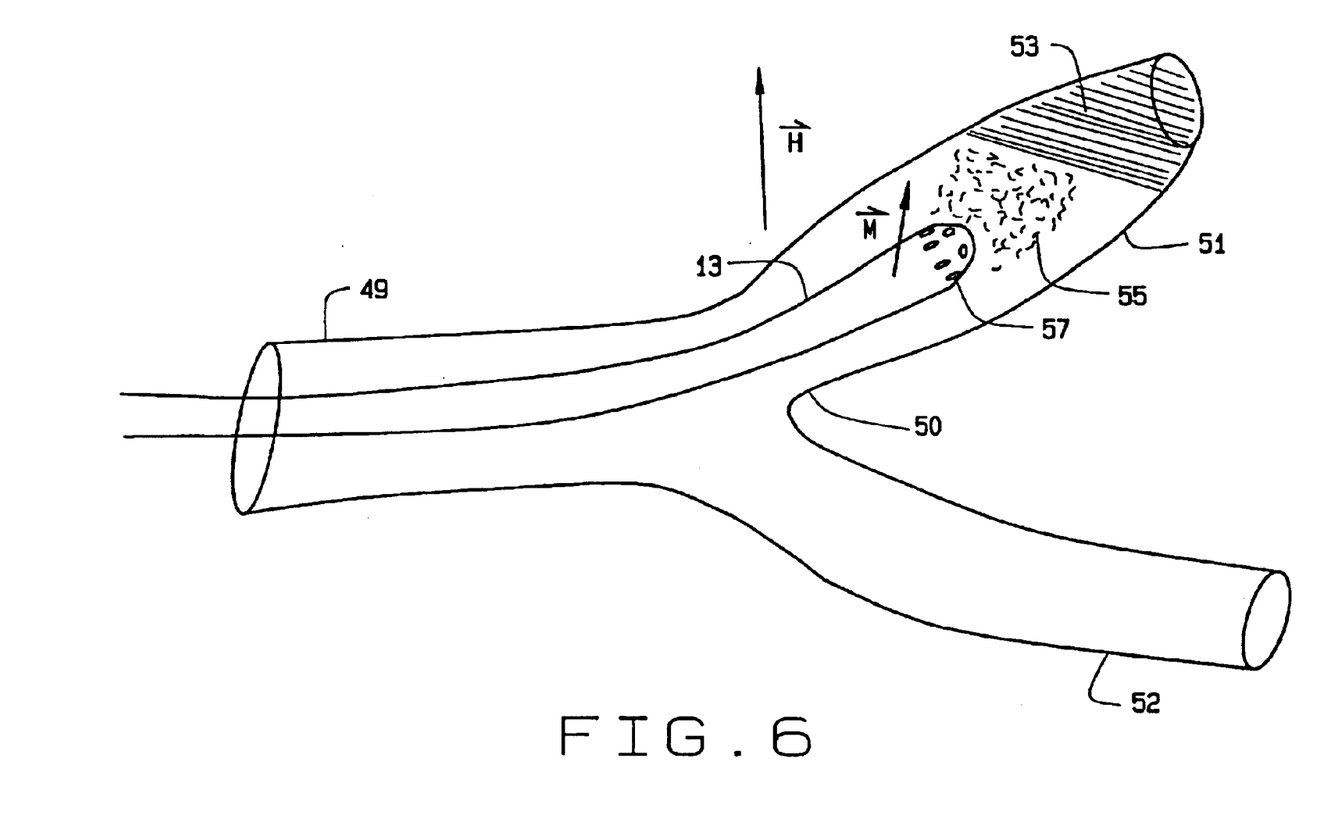
FIG. 6 is a schematic diagram showing the navigation of a catheter in the cerebrovasculature of a human patient in accordance with the method of this invention.

FIG. 6 shows a catheter 4 as it would be navigated inside of a vessel 49, located within a body part. The catheter 4, is advanced to a bifurcation 50 in the vessel 49 having a lower branch 52 and an upper branch 51. The catheter 4 is guided into the upper branch 51 of the vessel where it is to be used to treat a blockage 53 by infusing a thrombolytic agent 55 through the distal array of port holes 54 on this particular catheter. Many variations of this embodiment are possible for treating a variety of diseases, syndromes and conditions using different arrangements of the catheter 13 either inside of body ducts or lumens, or inside of the parenchymal tissues of a body part.

Figure 7A:
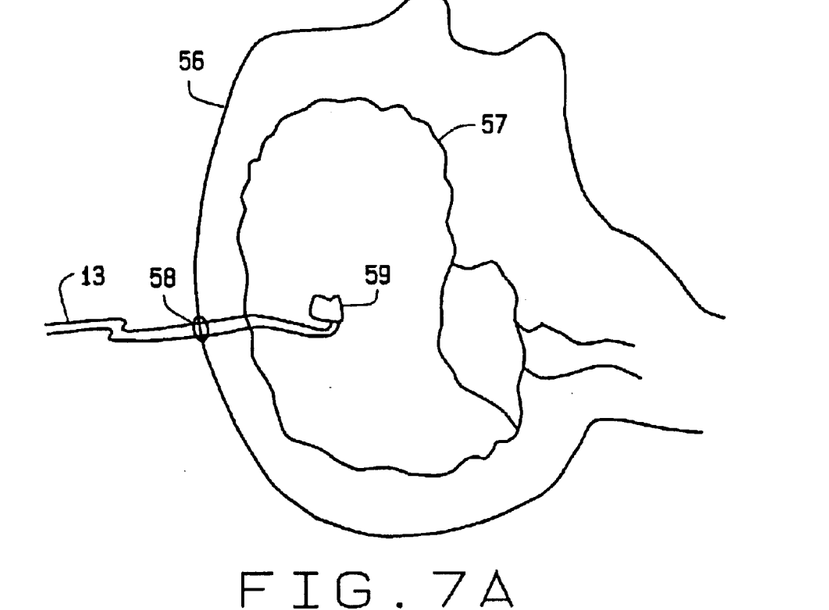
FIG. 7a is a schematic diagram of the head of a human patient, illustrating the navigation of a catheter through the intraparenchymal tissues of the brain of the patient.
Figure 7B:
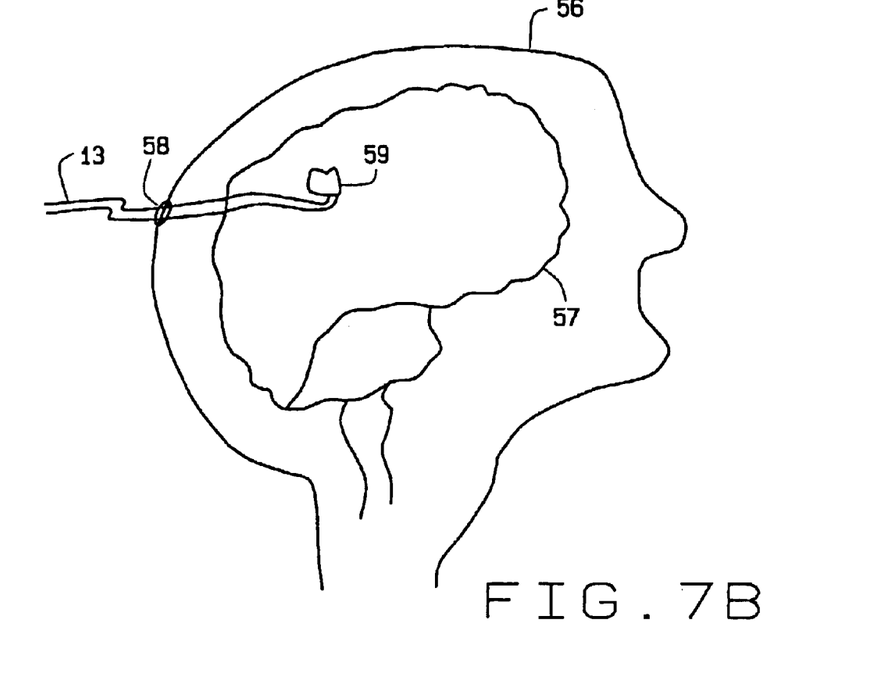
FIG. 7b is a schematic diagram of the head of a human patient, illustrating the navigation of a catheter through the intraparenchymal tissues of the brain of the patient.

FIG. 7a shows a catheter 4 as it would be used inside of a brain 57 of a patient 56. The catheter 13 has been inserted through a surgically placed burr hole 58 and navigated via magnetic stereotactic command of the triaxail coil means to reach a specified point on a lesion 59 within the brain 57. In the context of this drawing, the patient is lying flat on the gurney of a standard high-field MR machine and rests within the axial bore. The static magnetic field of the MRI is parallel to the long axis of the patient's body, hence the burr hole 58 is placed on the top of the patient's head in accordance with the access to the head permitted by the construction of the MRI. FIG. 7b contains the same elements as FIG. 7a. However, in the context of FIG. 7b the patient is located within the open bore of an interventional MR scanner and may not be lying flat but oriented at some angle with respect to the horizontal, possibly even vertically. This may permit or even require that the burr hole be placed occipitally or elsewhere on the skull.

Figure 8:
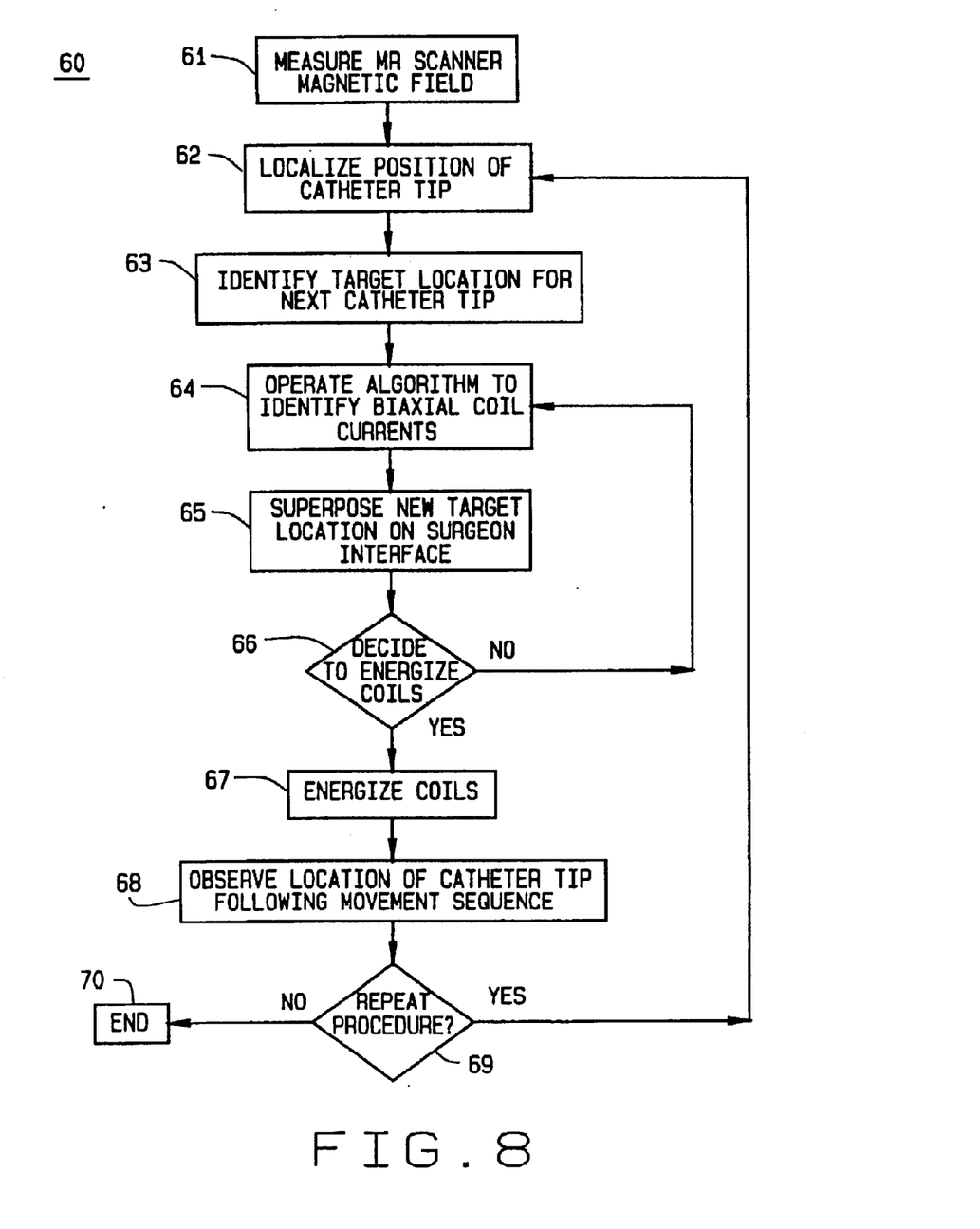
FIG. 8 is a flow chart of the method of navigating a medical device in accordance with the method of this invention.

FIG. 8 is a flow chart showing several of the steps needed to carry out a magnetic stereotaxis procedure using the triaxial coil means inside of a catheter within a body part of a patient who is located in a MR scanner. At 61 the MR scanner magnetic field is measured. At 62 the position of the catheter tip is localized. At 63 the target location for the next catheter step is identified by the physician. This can be done on a user-friendly computer interface. At 64 a mathematical algorithm is executed to identify the currents in the triaxial coil currents. At 65 the new target location is displayed on the interface. At 66 the physician decides whether to energize the coils. If the physician decides not to energize the coils, the process turns to step 64 where a new set of coil currents are calculated. If the physician decides to energize the coils, at 67 the coils are energized and at 68 the physician observes the location of the tip following the movement sequence. At 69, the physician decides whether the catheter is at its desired location, if it is, at 70 the procedure is over; if the catheter is not at its desired position the process resumes at 62.

Figure 9:
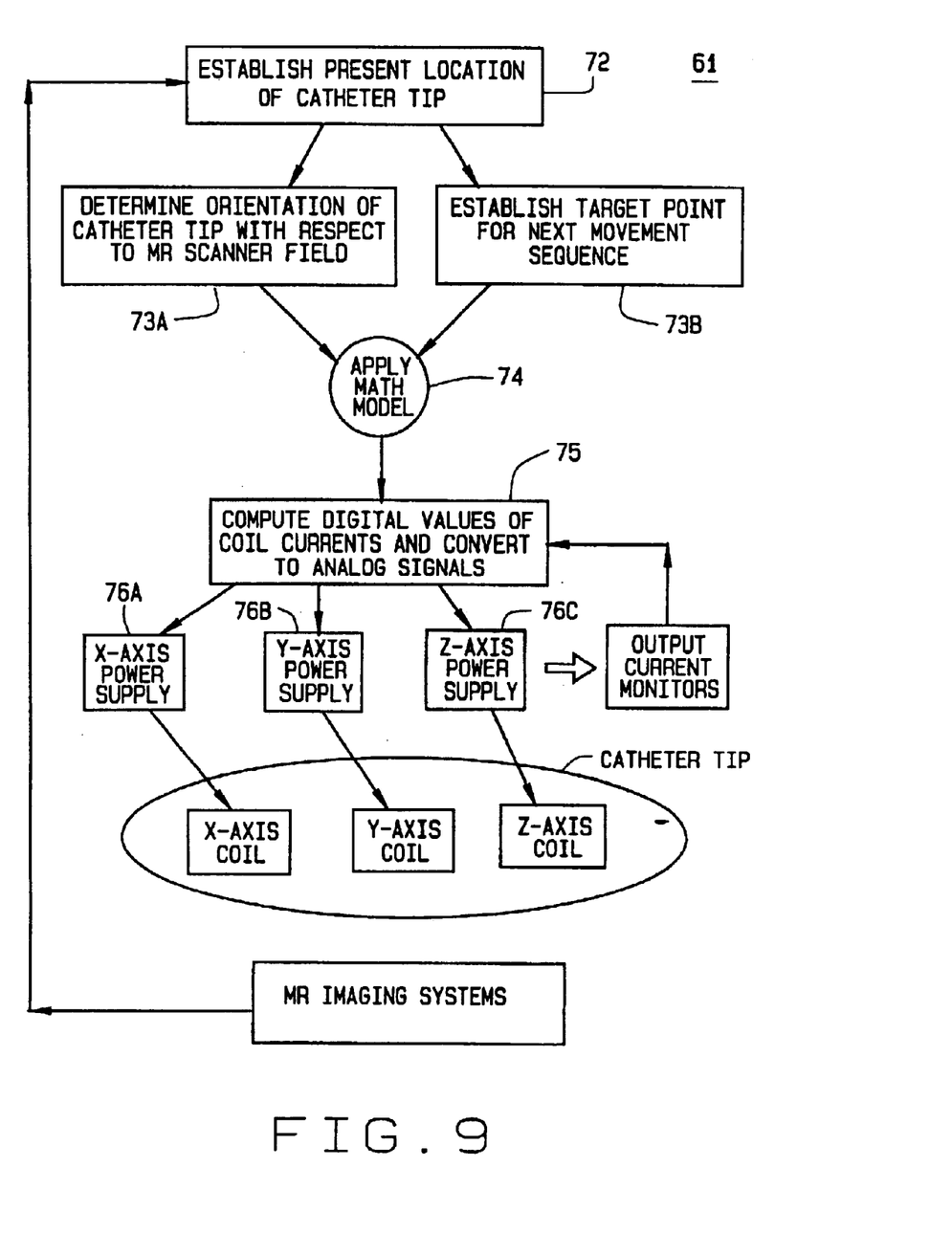
FIG. 9 is a flow chart of the computational algorithm that could be used to execute the method of navigating a medical device in accordance with the method of this invention.

FIG. 9 shows a flow chart 71 that identifies several of the steps needed to regulate the coil currents in the triaxial coil 23 that is being used to steer a catheter in the form of magnetic stereotaxis that is the subject of the present invention. At 72 the present location of the catheter tip is determined. At 73a the orientation of the catheter tip with respect to the MR scanner field is determined, and at 73b the target point for the next movement sequence is established. At 74 the math model is applied, and at 75 digital values of coil current are computed, and the digital values are converted to analog signal. At 76a, 76b and 76c the analog signals are applied to the x-axis, y-axis, and z-axis coils. Also the output signals are fed back to the coil current computation step.

Figure 10A:
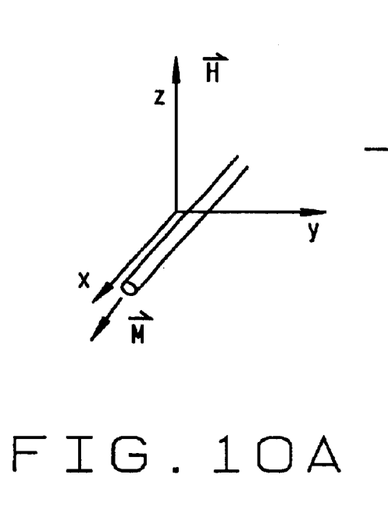
FIGS. 10a, 10b, 10c and 10d are schematic view of successive steps in a method for accomplishing rotation about the H field direction using compound rotations in accordance with the principles of this invention.
Figure 10B:
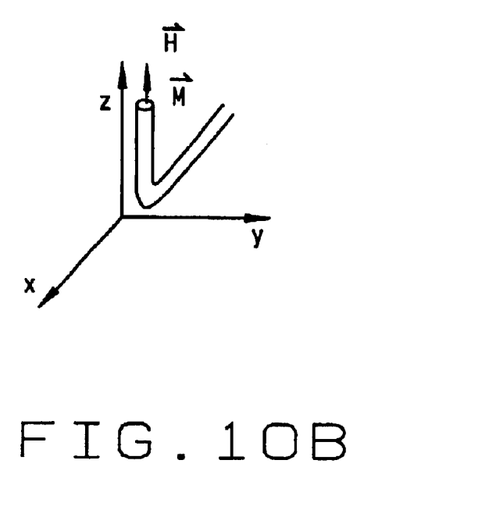
Figure 10C:
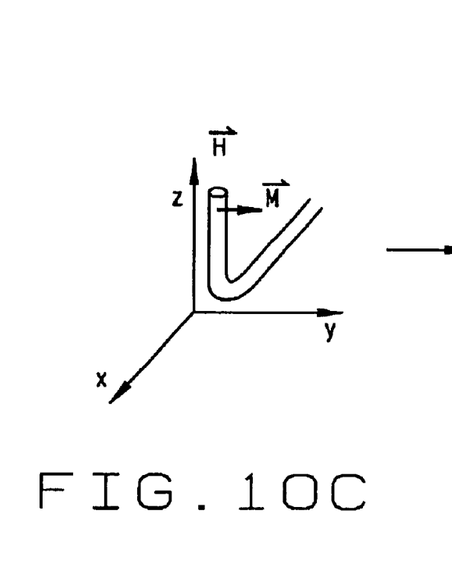
Figure 10D:
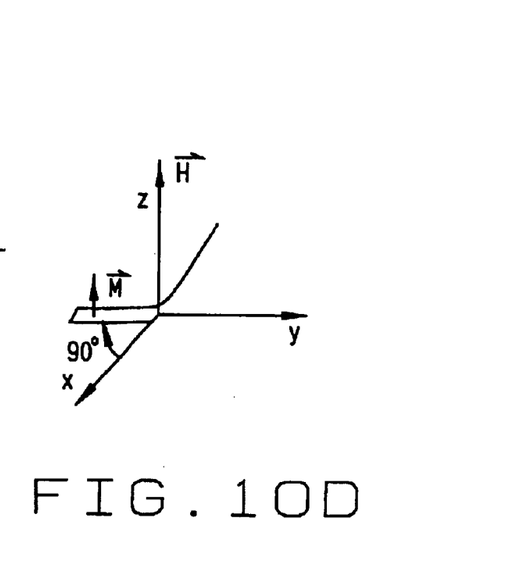
Figure 11A:
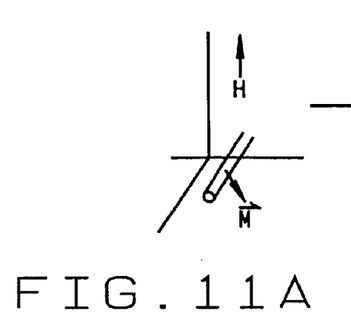
FIGS. 11a, 11b, 11c and 11d are schematic views of successive steps in a method for accomplishing rotation about the H field direction using compound rotations in accordance with the principles of this invention.
Figure 11B:
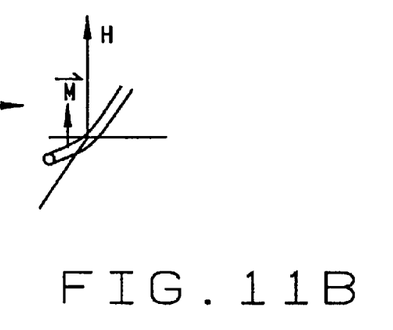
Figure 11C:
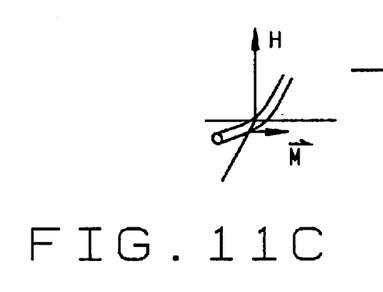
Figure 11D:
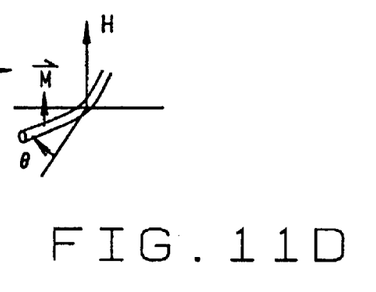
Figure 12A:
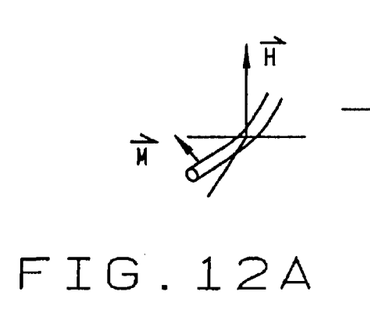
FIGS. 12a and 12b are schematic diagrams illustrating unidirectional torque applied to a catheter, for example to relieve strain built up in the catheter due to multiple torques applied in one direction.
Figure 12B:
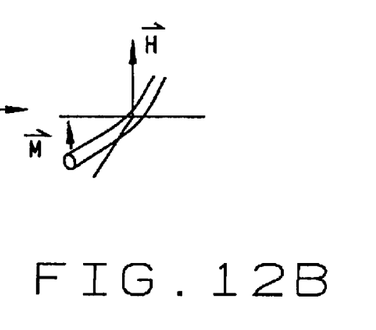

FIGS. 10a–10d illustrate a method for rotation of a catheter 4 about the MR magnetic field axis, employing two successive rotations about the orthogonal x and y axes. As shown in FIG. 10a, a magnetic moment is created at the distal end of the catheter so that the catheter bends out of the x-y plane to be parallel with the z-axis (corresponding to the local magnetic field direction), shown in FIG. 10b. As shown in FIG. 10c, a magnetic moment is created at the distal end of the catheter so that the catheter bends out of the x-z plane to be parallel to the y-axis. Thus rotation about the magnetic field direction (z direction) is possible by successive rotations about the y-axis and then the x-axis. FIGS. 11a–11d show how rotation about the field axis is accomplished by a series of incremental rotations out of the x-y plane. As shown in FIG. 11a, a magnet moment is created at the distal end of the catheter so that the catheter bends out of the x-y plane to an angle in the x-z plan (z corresponding to the local magnetic field direction), shown if FIG. 11b. As shown in FIG. 11c, a magnetic moment is created at the distal end of the catheter so that the catheter bends out of the x-z plane back into the x-y plane to an angle with respect to the x-axis. Thus, rotation about the magnetic field direction (z direction) is possible by successive rotations about the y-axis and then the x-axis. FIGS. 12a–12b show a method to apply torque about the axis of the catheter, which can be used, for example, to relieve strain built up in the multiple rotations used in FIGS. 10a–d and 11a–d. As shown in FIG. 12a a magnetic moment is created in the distal tip of the catheter that in the applied magnetic field causes the catheter to rotate about its longitudinal axis to "unwind" from twisting caused by the compound navigations shown and described in conjunction with FIGS. 10 and 11.

We claim:

1. A method of navigating a medical device having a variable magnetic moment within an operating region within a patient, using an MR imaging device, the method comprising:
applying a static magnetic field to the operating region with an external magnet of an MR imaging device;
energizing at least one electromagnetic coil overlapping another electromagnetic coil of the medical device to create temporary magnetic moments in the medical device to change the orientation of the medical device with respect to the static magnetic field, and orient the medical device in a selected direction within the operating region.

2. The method according to claim 1 further comprising the step of moving a patient to vary the direction of the static magnetic field applied to the operating region by the external magnet of an MR imaging device to change the orientation of the medical device.

3. The method according to claim 1 wherein energizing at least one electromagnetic coil comprises reducing an effect of magnetic field coupling on the energizing using a twisted pair.

4. The method according to claim 1 wherein the MR imaging device is used to image the operating region in the patient's body between navigations.

5. The method according to claim 1 in which the medical device comprises at least one set of three current carrying coils, and the step of creating temporary magnetic moments in the medical device comprises apply current to one or more of the current carrying coils.

6. The method according to claim 5 wherein there are at least two sets of three current carrying coils.

7. The method according to claim 1 in which the medical device comprises at least one set of three current carrying coils, and wherein the coils are used to receive signals during MR imaging to determine at least one of the location and orientation of the medical device.

8. The method according to claim 1 in which the medical device comprises at least one set of three current carrying coils, and wherein the coils are used to transmit and/or receive signals during MR imaging to enhance imaging adjacent the medical device.

9. The method according to claim 5 wherein the coils are mutually orthogonal.

10. The method according to claim 5 further comprising actively removing heat from the medical device generated by the current carrying coils.

11. The method according to claim 10 wherein heat is removed by circulating a cooling medium with the medical device.

12. The method according claim 10 wherein heat is removed using thermoelectric devices.

13. The method according to claim 10 wherein heat is removed using a heat pipe.

14. A method of navigating a medical device within an operating region in the body of a patient, the medical device having at least one coil therein, the method comprising:
establishing a navigating magnetic field in the operating region with an MR imaging device outside of the patient's body;
selectively energizing the at least one coil in the medical device to create a magnetic moment in the medical device and creating a torque tending to align the magnetic moment of the magnetic medical device with the applied magnetic field; and
actively removing heat from the at least one coil through the medical device.

15. The method according to claim 14 further comprising varying the direction and/or intensity of the applied magnetic field applied by the MR imaging device to orient the medical device.

16. The method according to claim 14 wherein the step of selectively energizing the at least one coil comprises applying electrical energy in pulses to the at least one coil in the medical device.

17. The method according to claim 16 wherein the medical device is flexible and has a characteristic recovery time in which the device recovers from being flexed, and wherein the time between pulses in less than the characteristic recovery time of the medical device.

18. A method of navigating a medical device having a variable magnetic moment within an operating region within a patient, using an MR imaging device, the method comprising:
applying a static magnetic field to the operating region with an external magnet of an MR imaging device;
creating temporary magnetic moments in the medical device to change the orientation of the medical device with respect to the static magnetic field, and orient the medical device in a selected direction within the operating region;
wherein the medical device comprises at least two sets of three current carrying coils, and creating temporary magnetic moments in the medical device comprises applying current to one or more of the current carrying coils.

19. A method of navigating a medical device having a variable magnetic moment within an operating region within a patient, using an MR imaging device, the method comprising:
applying a static magnetic field to the operating region with an external magnet of an MR imaging device; and
applying electrical energy to create temporary magnetic moments in one or more coils in the medical device to change the orientation of the medical device with respect to the static magnetic field, and orient the medical device in a selected direction within the operating region; and
actively controlling heat resulting from applying the electrical energy in the medical device.

20. The method of claim 19, wherein actively controlling heat comprises applying the electrical energy in pulses to at least one coil.

21. The method of claim 19, wherein actively controlling heat comprises:
carrying a heat exchange medium into the medical device; and
cooling the heat exchange medium leaving the medical device.

* * * * *